US00PP29769P3

(12) United States Plant Patent
Sidhu

(10) Patent No.: US PP29,769 P3
(45) Date of Patent: Oct. 23, 2018

(54) ***NANDINA* PLANT NAMED 'NANSID3'**

(50) Latin Name: *Nandina domestica*
Varietal Denomination: NanSid3

(71) Applicant: Gurjit Sidhu, Mission (CA)

(72) Inventor: Gurjit Sidhu, Mission (CA)

( * ) Notice: Subject to any disclaimer, the term of this patent is extended or adjusted under 35 U.S.C. 154(b) by 0 days.

(21) Appl. No.: 15/530,724

(22) Filed: Feb. 21, 2017

(65) Prior Publication Data

US 2017/0311506 P1 Oct. 26, 2017

(30) Foreign Application Priority Data

Apr. 26, 2016 (CA) ..... PBR 16-8902

(51) Int. Cl.
*A01H 5/00* (2018.01)
*A01H 5/12* (2018.01)

(52) U.S. Cl.
USPC ..... Plt./235
CPC ..... *A01H 5/12* (2013.01)

(58) Field of Classification Search
USPC ..... Plt./235
CPC ..... A01H 5/02
See application file for complete search history.

(56) References Cited

PUBLICATIONS http://members.tripod.com/hatch_1/orocbook3.pdf; OROC Open Registration of Cultivars International Register of Ornamental Plant Cultivars: Woody Plants: N-Z Book III: Nov. 2016; 2 pages.*

* cited by examiner

*Primary Examiner* — Kent L Bell
(74) *Attorney, Agent, or Firm* — Penny J. Aguirre

(57) ABSTRACT

A new cultivar of *Nandina domestica* named 'NanSid3', characterized by its foliage with new growth that is reddish in color, its compact, upright mounding plant habit with dense foliage, and its fall color that is red in color.

2 Drawing Sheets

Botanical classification: *Nandina domestica.*
Variety denomination: 'NanSid3'.

CROSS REFERENCE TO A RELATED APPLICATION

This application is co-pending with a U.S. Plant Patent Application filed for a plant derived from the same breeding program that is entitled *Nandina* Plant Named 'NanSid6' (U.S. Plant patent application Ser. No. 15/530,719).

BACKGROUND OF THE INVENTION

The present invention relates to a new and distinct cultivar of *Nandina domestica* and will be referred to hereafter by its cultivar name, 'NanSid3'. 'NanSid3' is a new cultivar of heavenly bamboo shrub grown for use as a landscape plant.

The new cultivar was discovered as a branch mutation by the Inventor in 2010 in Mission, British Columbia, Canada. The new cultivar arose as a naturally occurring branch mutation of *Nandina domestica* 'Gulfstream' (U.S. Plant Pat. No. 5,656) that was growing in a container at his nursery.

Asexual reproduction of the new cultivar was first accomplished under the direction of the inventor by tissue culture of meristematic tissue in 2011 in Mission, British Columbia, Canada. Asexual propagation by tissue culture and stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'NanSid3' as a unique cultivar of *Nandina.*

1. 'NanSid3' exhibits foliage with new growth that is reddish in color.
2. 'NanSid3' exhibits a compact, upright mounding plant habit with dense foliage.
3. 'NanSid3' exhibits fall foliage that is red in color.

'Gulfstream', the parent plant of 'NanSid3', is similar to 'NanSid3' in growth rate and plant habit. 'Gulfstream' differs from 'NanSid3' in having foliage with new growth that is bronzy orange in color. 'NanSid3' can be most closely compared to the cultivars 'NanSid6' and 'Little Flick' (U.S. Plant Pat. No. 26,276). 'NanSid6' is similar to 'NanSid3' in growth rate and plant habit. 'NanSid6' differs from 'NanSid3' in having foliage with new growth that is more purple in color and in having more finely dissected foliage. 'Little Flick' is similar to 'NanSid3' in having red foliage. 'Little Flick' differs from 'NanSid3' in having a larger plant size in height and width.

BRIEF DESCRIPTION OF THE DRAWINGS

The accompanying colored photographs illustrate the overall appearance and distinct characteristics of two year-old plants of the new *Nandina* as grown outdoors in 1-gallon containers in St. Thomas, Ontario, Canada.

The photograph in FIG. 1 illustrates the overall plant habit and new foliage and mature foliage of 'NanSid3' in summer.

Figure 1:
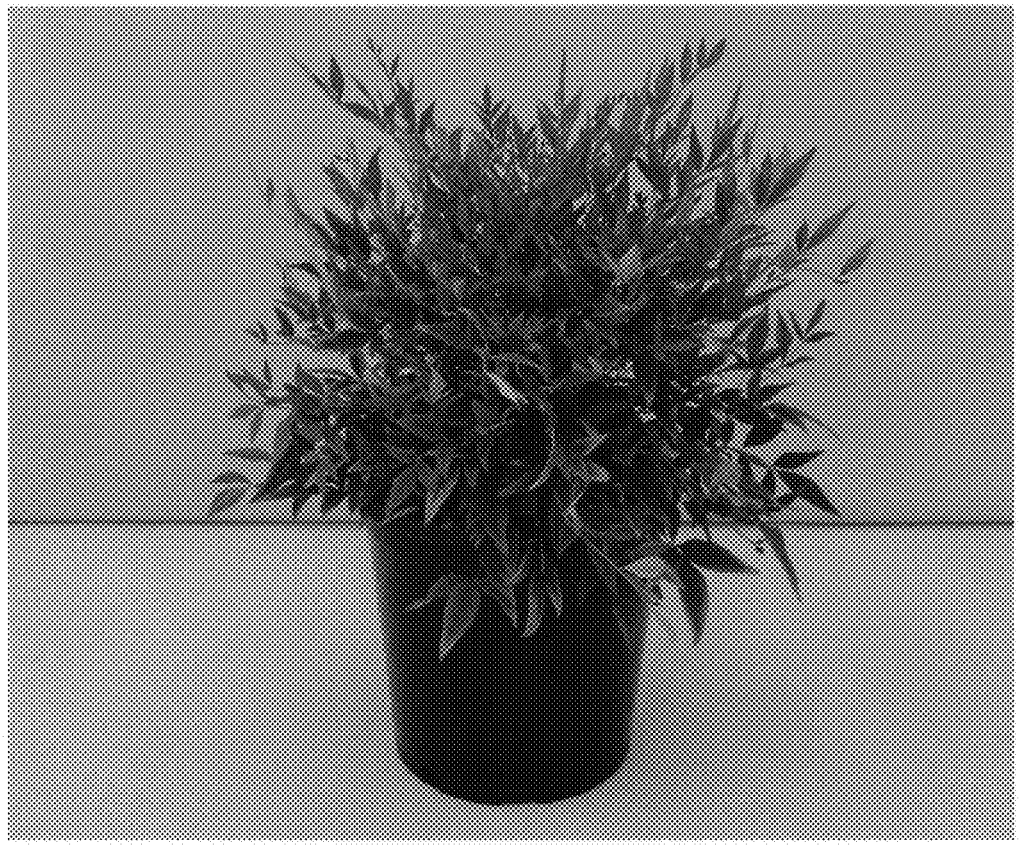
Figure 2:
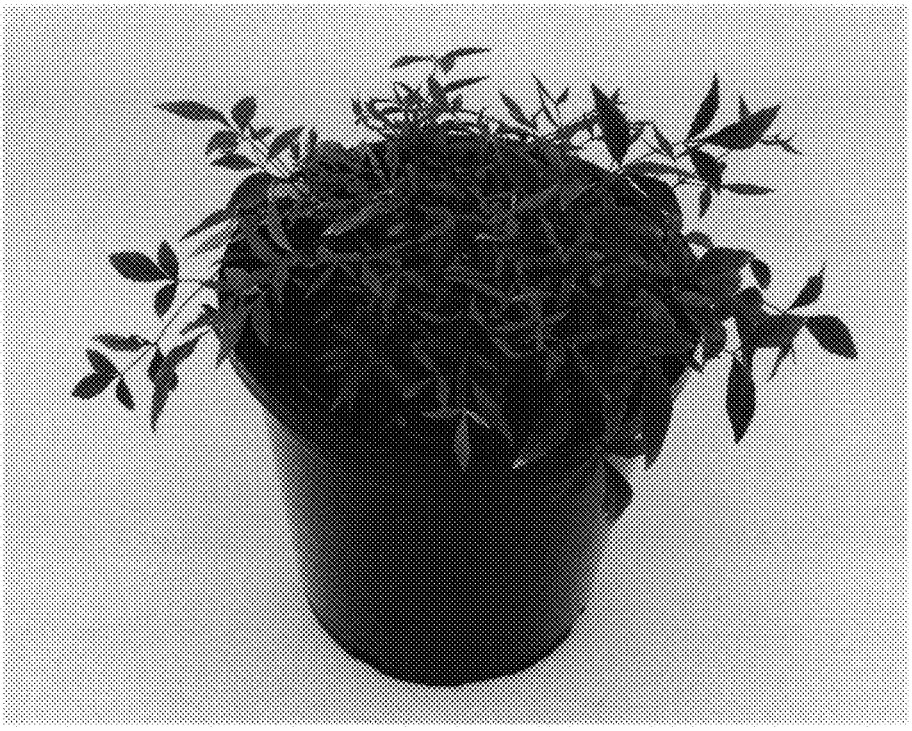

The photograph in FIG. 2 provides a view of the new foliage in spring of 'NanSid3'.

Figure 3:
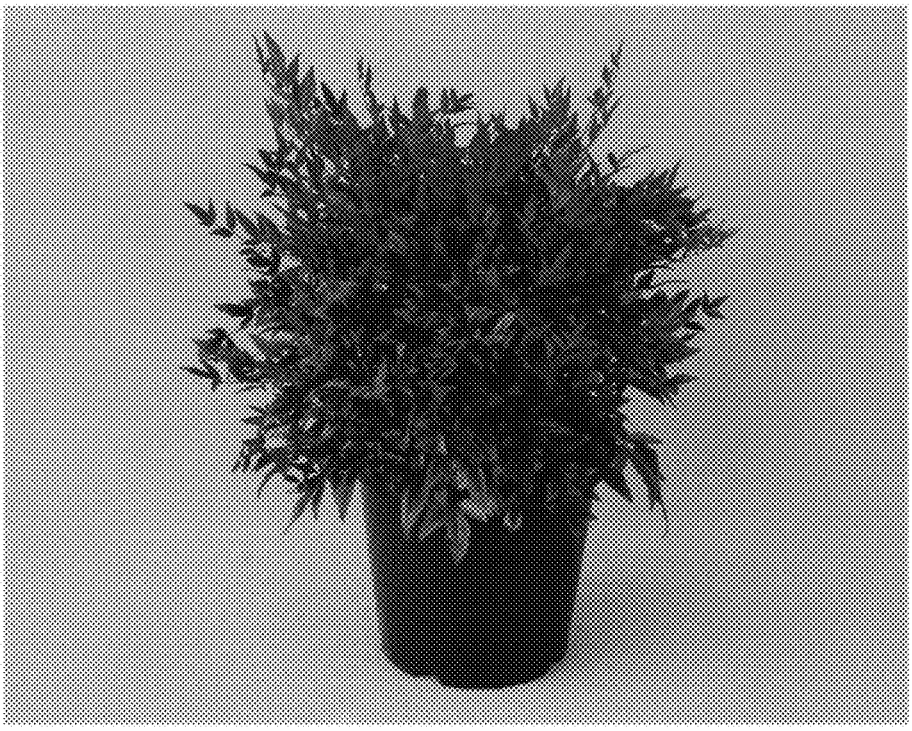

The photograph in FIG. 3 provides a view of the fall foliage of 'NanSid3'.

The colors in the photographs are as close as possible with the digital photography techniques utilized and the color values cited in the detailed botanical description accurately describe the colors of the new *Nandina*.

DETAILED BOTANICAL DESCRIPTION

The following is a detailed description of a 2 year-old plant of the new cultivar as grown outdoors in a 1-gallon container in St. Thomas, Ontario, Canada. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Plant type*.—Semi-evergreen and evergreen shrub.

*Plant habit*.—Compact, upright mounding habit with dense foliage.

*Height and spread*.—Reaches about 32 cm in height and 36 cm in width as a 2 year-old plant in a one-gallon container and 1 m in height and 0.9 m in width in the landscape.

*Diseases and pests*.—No susceptibility or resistance to diseases or pests has been observed.

*Cold hardiness*.—At least in U.S.D.A. Zone 6a.

*Root description*.—Fibrous, outward spreading by underground rhizomes has not been observed.

*Propagation*.—Stem cuttings and tissue culture.

*Root development*.—6 to 8 weeks for a rooted cutting and about 4 months to develop a young plant from a rooted cutting.

*Growth rate*.—Moderate to slow.

Stem (cane) description:

*Stem shape*.—Rounded, comprised of clasping petioles.

*Stem strength*.—Strong.

*Stem color*.—Closest to N199A.

*Stem size*.—Average of 5.9 cm in length and 5.6 cm in width.

*Stem surface*.—Smooth.

*Stem aspect*.—Upright.

*Internode length*.—1.9 cm.

*Branching*.—Branches freely from basal buds.

Foliage description:

*Leaf shape*.—Rhomboidal in outline.

*Leaf division*.—Mostly tri-pinnate, leaflets occur in opposite pairs, with an average of 50 leaflets per leaf.

*Leaf arrangement*.—Alternate.

*Leaf attachment*.—Petiolate.

*Leaflet base*.—Attenuate.

*Leaflet apex*.—Acute.

*Leaflet fragrance*.—None.

*Leaflet venation*.—Pinnate, not conspicuous, matches leaflet color on upper and lower surface, mid rib is slightly protruding on lower surface.

*Leaflet margins*.—Entire.

*Leaflet surface*.—Glabrous on upper and lower surface.

*Leaflet attachment*.—Sessile.

*Leaf size*.—Average of 27.9 cm in length and 26.3 cm in width.

*Leaflet size*.—Average of 5.7 cm in length and 1.6 cm in width.

*Leaflet shape*.—Elliptic and lanceolate.

*Leaflet color*.—New growth in spring; 183A to 183B on upper surface and 183B on lower surface, as leaf expands the color gradually changes to N144A and 144A on upper surface and 144B and 144C on lower surface; summer color; outer new leaves in full sunlight close to 1C heavily suffused with 50A to 50B on upper surface and 154D suffused with 51B on lower surface, mature leaves in shaded areas; mainly N137A on upper surface and 137C on lower surface, fall color; outer leaves vary in color from 45C, 181B and N34A on upper surface and 146B suffused with 180C to 180D on lower surface, inner leaves mainly 146B on upper and lower surfaces.

*Petioles*.—Average of 4.6 cm in length and 1.2 mm in diameter, surface is glabrous and dull, clasping base is 2.0 cm in length and 0.7 cm in width, color on new growth in spring; 183A, summer; outer leaves 45A, inner leaves 144B, fall; 178A.

*Petiolules*.—Primary; average of 4.3 cm in length and 0.5 mm in width, surface is glabrous and dull, secondary; average of 2.5 cm in length and 0.3 mm in width, surface is glabrous and dull, similar coloration as petioles.

Inflorescence description: Blooms are very rare, typically plants of the new cultivar do not bloom.

It is claimed:

1. A new and distinct cultivar of *Nandina* plant named 'NanSid3' as herein illustrated and described.

* * * * *